United States Patent [19]
Baumgartner et al.

[11] Patent Number: 6,054,618
[45] Date of Patent: Apr. 25, 2000

[54] PREPARATION OF N-PHENYL-1-NAPHTHYLAMINE

[75] Inventors: Hanspeter Baumgartner, Krefeld; Lutz Frohn, Erkrath; Alexander Klausener, Pulheim; Frank Arndt, Krefeld, all of Germany

[73] Assignee: Bayer Aktiengesellschaft, Leverkusen, Germany

[21] Appl. No.: 09/209,408

[22] Filed: Dec. 10, 1998

[30] Foreign Application Priority Data

Dec. 17, 1997 [DE] Germany .................. 197 56 146

[51] Int. Cl.$^7$ .................................. C07C 211/00
[52] U.S. Cl. ............................................. 564/429
[58] Field of Search ............................... 564/429

[56] References Cited

U.S. PATENT DOCUMENTS 5,658,866  8/1997  Yoshida et al. .................. 508/503

FOREIGN PATENT DOCUMENTS 241853  11/1911  Germany .

OTHER PUBLICATIONS

Ullmanns Encyclopaedia of Industrial Chemistry, 4th ed., vol. 17, (month unavailable) 1979, p. 107.

H.E. Fierz–David and L. Blangley, Farbenchemie, 8th ed., p. 171, (month unavailable) 1952.

J. Prakt Chem 89, I (month unavailable) 1914.

*Primary Examiner*—Paul J. Killos
*Attorney, Agent, or Firm*—Joseph C. Gil; Lyndanne M. Whalen; Diderico van Eyl

[57] ABSTRACT

N-phenyl-1-naphthylamine can be prepared by reacting aniline and 1-naphthylamine in the liquid phase at 100–400° C. at a reaction pressure which is higher than atmospheric pressure. Boron and fluorine-containing catalysts, mono or polysulfonic acids, iodine, $PCl_3$, $PCl_5$, or $POCl_3$, for example, may be used as catalysts.

19 Claims, No Drawings

PREPARATION OF N-PHENYL-1-NAPHTHYLAMINE

Foreign priority in claimed, Germany Application No. 19756146.2 filled Dec. 17, 1997

The present invention relates to a process for preparing N-phenyl-1-naphthylamine (phenyl-α-naphthylamine) of the Formula (I)

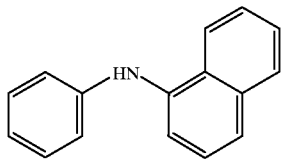

(I)

by reacting aniline with 1-naphthylamine, wherein the reaction is performed in the presence of a catalyst in the condensed phase and under a pressure which is higher than atmospheric pressure.

N-phenyl-1-naphthylamine is used, for example, as an ageing or oxidation prevention agent for rubber and for mineral oil products (Ullmänns Encyklopadie der technischen Chemie, 4th edition, vol. 17, p. 107, Verlag Chemie, Weinheim 1979). This compound is also used in the dye sector. Thus the dye victoria blue, a diphenyl-naphthylmethane derivative, is obtained from N-phenyl-1-naphthylamine (H. E. Fierz-David and L. Blangley, Farbenchemie 8th edition, p. 171, Springer-Verlag, Vienna 1952). Derivatives of N-phenyl-1-naphthylanine, which are prepared either from this compound itself or in an analogous way to this compound, are also of interest as components in lubricants (EP 716 141).

According to H. E. Fierz-David and L. Blangley, Farlbenchemie, 8th edition, p. 171, Springer-Verlag, Vienna 1952, N-phenyl-1-naphthylamine is obtained in yields of 86–91% of the theoretical yields by reacting aniline and 1-naphthylamine at temperatures of 195–215° C. under atmospheric pressure, wherein sulfanilic acid is used as catalyst. The process requires long reaction times. According to a procedure described in DE-PS 241 853, and in J. Prakt. Chem. 89, 1(1914), N-phenyl-1-naphthylamine is obtained by reacting aniline and 1-naphthylamine at temperatures of 225–250° C. in the presence of catalytic amounts of iodine at atmospheric pressure. The reaction yields described are much lower than those in the process mentioned above and the reaction times are also disadvantageously long. According to J. Prakt. Chem. 89, 1(1914), N-phenyl-1-naphthylamine can be obtained by reacting 1-naphthol with aniline at temperatures between 180 and 200° C., also in the presence of catalytic amounts of iodine at atmospheric pressure. The yields however reach only 35–40% of the theoretical yields which seems to make this variant much more unfavourable than those described above.

A common feature of all the processes mentioned is that relatively large amounts of undesired secondary products, such as for example diphenylamine, N-phenyl-2-naphthylamine and 2-naphthylamine are formed during the course of reaction. In particular, the last-named compounds N-phenyl-2-naphthylamine and 2-naphthylamine may be produced basically by isomerisation of N-phenyl-1-naphthylamine which has already been formed and unreacted 1-naphthylamine, specifically as a function of the reaction conditions and catalyst used. Apart from the fact that the production of this type of undesired secondary product has a negative impact on the economic viability of the particular process of preparation due to the associated loss of material and the increased separation costs required in order to isolate pure N-phenyl-1-naphthylamine, there is a further consideration in that 2-naphthylamine in particular has highly toxic properties and its production must therefore be excluded as far as possible.

Thus there is the object of finding an economically viable process for the highly selective preparation of N-phenyl-1-naphthylamine in which the production of undesired secondary products, in particular however the production of 2-naphthylamine, is largely excluded, which enables the recycling of any catalyst used and which can be operated with economically satisfactory reaction times and space time yields.

It has now been found that N-phenyl-1-naphthylamine can be obtained in high yields and with exceptional selectivity when aniline and 1-naphthylamine are reacted with each other in the presence of a catalyst under a reaction pressure which is higher than atmospheric pressure. This is surprising insofar as aniline reacts with itself at high pressures to produce diphenylamine. Also surprising was the observation that some of the catalysts used according to the invention, namely those containing fluorine and optionally boron, can be recovered in a simple manner, that is without purification or further processing, by aqueous extraction of the reacted reaction mixture. Catalysts recycled in this way can be returned to the reaction without any unacceptable negative consequences on the conversion and selectivity. In view of the prior art described above this beneficial result could not have been expected. Rather, it would be expected that the reaction of aniline and 1-naphthylamine would be associated with the production of relatively large amounts of undesired secondary products and a loss of the catalyst after performing the reaction. In particular it would have been expected that reaction of 1-naphthylamine with aniline under pressure would lead to the production of significant amounts of diphenylamine which would considerably impair the economic viability of the process.

A process for batchwise or continuous preparation of N-phenyl-1-naphthylamine by reacting aniline and 1-naphthylamine in the condensed phase at 100–400° C. was found which is characterised in that the reaction is performed in the presence of a catalyst and at a reaction pressure which is higher than atmospheric pressure.

Basically quite different systems can be used as catalysts for the process according to the invention for preparing N-phenyl-1-naphthylamine. A few typical catalyst systems are mentioned by way of example in the following.

a) Fluorine-containing Catalyst Systems

Either freshly prepared catalysts or batches of catalyst which have been recovered during the course of processing reaction mixtures, for example, may be used. Basically it is also possible to use mixtures of recovered and freshly prepared catalyst. The reaction product which is obtained from the reaction of hydrogen fluoride, boric acid and aniline and/or 1-naphthylamine is preferably used as a typical fluorine-containing catalyst for the process according to the invention in the event of using fresh catalyst batches. This is a salt-like product of the formula

[A][B] (II), in which

A represents the cations $[H]^+$, $[NH_4]^+$, $[phenyl\text{-}NH_3]^+$, $[(1\text{-naphthyl})\text{-}NH_3]^+$, $[phenyl\text{-}NH_2\text{-}phenyl]^+$ or $[phenyl\text{-}NH_2\text{-}(1\text{-naphthyl})]^+$, preferably for the cations

[H]$^+$, [NH$_4$]$^+$, [phenyl-NH$_3$]$^+$ and [(1-naphthyl)-NH$_3$]$^+$ and in particular for the cations [NH$_4$]$^+$ and [phenyl-NH$_3$]$^+$ and B represents anions of the type [B(OH)$_n$F$_{4-n}$]$^-$, in which n can take on integer values from 0 to 4 and preferably represents the anion [BF$_4$]$^-$.

Important individual compounds of the formula (II) are for instance [NH$_4$]$^+$ [BF$_4$]$^-$ and [phenyl-NH$_3$]$^+$ [BF$_4$]$^-$.

In practice, the catalyst mixtures active within the reaction according to the invention may contain components which differ from those corresponding to the general formula (II), but whose composition is adjusted in accordance with the provisos of stoichiometric ratio and the basicities and dissociation constants of the optionally contributing cationic major components water, ammonia, aniline, 1-naphthylamine and N-phenyl-1-naphthylamine and which in general contain proportions of the components water, ammonia, aniline and/or 1-naphthylamine and optionally other aromatic diamines also in unprotonated form. These mixtures are present in a homogeneously dissolved form under the reaction conditions for preparing N-phenyl-1-naphthylamine and thus act in their entirety as a homogeneous catalyst system.

Fresh batches of the catalyst according to the invention are generally prepared using methods known to a person skilled in the art. Thus for instance it is possible to use aqueous solutions of ammonium tetrafluoroborate as fresh catalyst. In a preferred embodiment of the process according to the invention the preparation of fresh batches of the catalyst according to the invention is performed in physically separated, special reaction vessels. For example, the fluorine-containing catalyst is prepared by reacting, as reaction components, aniline and/or 1-naphthylamine, boric acid and hydrogen fluoride. Aniline, boric acid and hydrogen fluoride are preferably reacted together. Freshly supplied aniline and/or 1-naphthylamine is preferably used for preparation of the fluorine-containing catalyst. It may also be of advantage, however, to use recovered aniline and/or 1-naphthylamine produced during the processing of spent reaction mixtures.

The boric acid used to prepared the fluorine-containing catalyst is preferably used as a solid. Basically, however, it is also possible, and may optionally be of advantage, to use the boric acid as a molten material, as a solution or as a slurry, for example in water and/or aniline.

The hydrogen fluoride used to prepare the fluorine-containing catalyst is generally used as a pure substance or as an aqueous solution. In a preferred embodiment, the hydrogen fluoride required is used as a concentrated aqueous solution. Basically, however, other methods of addition are possible such as, for example, the introduction of gaseous or liquified pure hydrogen fluoride.

To prepare the fluorine-containing catalyst, the contributing components are used in the ratio by weight of aniline and/or 1-naphthylamine to boric acid to hydrogen fluoride= (100 to 2000):(50 to 250):(50 to 250). Aniline, boric acid and hydrogen fluoride are preferably used in the ratio by weight of (300 to 1000):(100 to 150):(100 to 150). Basically, the individual components mentioned may be introduced in any order at all. In a preferred embodiment, the aniline is initially introduced, then boric acid is added and finally aqueous hydrofluoric acid is added.

The fluorine-containing catalyst is generally prepared at a reaction temperature between 0 and 250° C., preferably between 30 and 200° C., in particular between 70 and 150° C.

When preparing the fluorine-containing catalyst, it may be expedient to stir the mixture. Basically, however, it is also possible to omit any additional stirring. The heat of reaction being released during the course of preparing the fluorine-containing catalyst may be entirely or partly dissipated through external cooling. In general, the fluorine-containing catalyst is prepared at atmospheric pressure. Basically, however, it is also possible to perform the reaction at reduced or elevated pressure. The fluorine-containing catalyst prepared in this way is generally used in liquid form, without isolation or further purification, in the reaction for preparing N-phenyl-1-naphthylamine. Basically, however, it is also possible to evaporate the fluorine-containing catalyst to dryness under reduced pressure and to use the solid residue produced in this way as a catalytically active mixture in the reaction to prepare N-phenyl-1-naphthylamine.

b) Sulfonic Acids as Catalysts

Alternatively, mono, di or trisulfonic acids of the formula

$$R-(SO_3H)_n \hspace{2cm} (III)$$

may also be used in the context of the process according to the invention. In this case R represents linear or branched C$_1$–C$_{20}$-akyl groups or phenyl, naphthyl or pyridinyl groups which may be non-substituted or substituted with up to 3 further substituents, wherein hydrogen, straight-chain or branched C$_1$–C$_6$-alkyl groups, halogen, amino, straight-chain or branched C$_1$–C$_6$-alkylamino or di-(C$_1$–C$_6$-alkyl)amino groups, hydroxyl, straight-chain or branched C$_1$–C$_6$-alkoxy or carboxyl groups may be used as substituents and n represents the number 1, 2 or 3.

Preferably, mono- and disulfonic acids of the formula (III) are used in which R represents a C$_1$–C$_4$-alkyl group or a phenyl group which is unsubstituted or has up to two further substituents, wherein C$_1$–C$_4$-alkyl groups, fluorine, chlorine, bromine, amino or hydroxyl are suitable as substituents.

In particular, monosulfonic acids of the formula (III) are used in which R represents methyl or ethyl or a phenyl group which is unsubstituted or has one further substituent, wherein methyl, chlorine, bromine, amino, hydroxyl or carboxyl are suitable as the substituent.

Methane- and ethanesulfonic acids, benzenesulfonic acid, p-toluenesulfonic acid, 4chlorobenzenesulfonic acid, 4-bromobenzenesulfonic acid, 2-sulphobenzoic acid, o- m- and p-aminobenzenesulfoic acids may be mentioned by way of example.

c) Other catalysts

Basically, other catalysts may also be used, within the context of the process according to the invention, which catalyse the production of diarylamines from arylamines. Iodine, phosphorus trichloride, phosphorus oxychloride and phosphorus pentachloride may be mentioned by way of example. In the event of using catalysts which are labile to hydrolysis, however, recovery by aqueous extraction must be avoided.

The process according to the invention involves initially reacting aniline with 1-naphthylamine in the liquid phase in a suitable reactor in the presence of the chosen catalyst under a reaction pressure which is higher than atmospheric pressure. Water and/or, in the case of a fluorine-containing catalyst, an aqueous solution of the chosen catalyst is added to the liquid product mixture after the end of reaction and the mixture is separated into a largely aqueous and a largely organic liquid phase in an apparatus which is suitable for this purpose.

The liquid phase containing the major part of the organic material, which is substantially the reaction product N-phenyl-1-naphthylamine, unreacted starting material, that is aniline and 1-naphthylamine, and small amounts of secondary products, is isolated and taken to further processing. The largely aqueous phase containing the major part of the catalyst is also isolated. This may be entirely or partly discarded and/or, in the case of a fluorine-containing catalyst, entirely or partly used as a catalyst for performing the reaction of aniline and 1-naphthylamine in accordance with the invention without further purification or processing.

The liquid phase containing the major part of the organic material is optionally washed another one or more times by adding water and optionally one or more additional inorganic auxilliary agents and is then subjected to distillation. During final distillation of the reaction product, N-phenyl-1-naphthylamine is produced in a very pure form. Excess aniline and/or 1-naphthylamine is also obtained in a quality such that both components can be returned to the production process with no problem. Small amounts of distillation residues are taken to a residue recovery process or discarded.

The process according to the invention for preparing N-phenyl-1-naphthylamine may be performed basically in its entirety or in part in a batchwise or a continuous manner. The actual reaction of aniline and 1-naphthylamine is preferably performed in a batchwise manner; subsequent processing however may take place in a continuous manner.

The extraordinarily high efficiency and selectivity of the process according to the invention, in particular with regard to the absence of the undesired production of unacceptably high proportions of diphenylamine, is surprising and has not been previously described in the literature. In contrast, complicated procedures which are liable to break down and which involve secondary reactions such as, for example, the alternative processes discussed above have been proposed hitherto.

The reactants aniline and 1-naphthylamine used to prepare N-phenyl-1-naphthylamine are used in a molar ratio of 1:3 to 10:1, preferably 1:2 to 5:1 and in particular 1:1 to 3:1. The state of aggregation in which the individual components are introduced to the reaction is of no importance. In a preferred embodiment both aniline and 1-naphthylamine are introduced to the reaction in the liquid form. It may also be of advantage, however, to introduce 1-naphthylamine as a solid or aniline in the evaporated form to the reaction mixture.

A particularly advantageous variant of the process according to the invention for preparing N-phenyl-1-naphthylamine which is also provided by the invention, comprises introducing the reaction component 1-naphthylamine or a mixture of the reaction component 1-naphthylamine with some, about 5–40%, of the aniline required for reaction to the reaction vessel, after introducing the remaining amount of the reaction component aniline and the selected catalyst, during or after heating to the selected reaction temperature and after adjusting the selected pressure over the course of a specific period.

The catalyst or catalyst mixture introduced to the reaction for preparing N-phenyl-1-naphthylamine in accordance with the process according to the invention is used in an amount such that the molar ratio between the catalytically active components in the catalyst or the catalyst mixture and the total amount of the aniline and 1-naphthylamine used in the reaction is between 1:10 and 1:100,000, preferably between 1:25 and 1:10,000 and in particular between 1:50 and 1:1,000. The catalyst or catalyst mixture according to the invertion is generally used in the reaction mixture in liquid or solid form, as a pure substance, a solution or a slurry. In a particular embodiment, in the case of a fluorine-containing catalyst, the catalyst or catalyst mixture is introduced to the reaction according to the invention for preparing N-phenyl-1-naphthylamine after evaporating catalyst-containing solutions such as are obtained for instance during the preparation of fresh catalyst batches or during recovery of catalysts in the course of further processing of spent reaction mixtures, in the solid form as a catalytically active solid or catalytically active mixture of solids.

The reaction according to the invention for preparing N-phenyl-1-naphthylamine is performed in the pressure range above atmospheric pressure up to 15 bar, preferably at 1.5 to 10 bar, in particular at 1.5 to 5 bar. The reaction according to the invention for preparing N-phenyl-1-naphthylamine is performed in the temperature range between 100 and 400° C., preferably between 150 and 350° C., in particular between 180 and 300° C. To ensure the chosen temperature level, the reaction vessel is provided with the heat energy required via external and/or internal heating units.

The reaction mixture is thoroughly mixed during the course of the reaction according to the invention to prepare N-phenyl-1-naphthylamine. This may be achieved, for example, by stirring units, by external or internal circulating pump devices or in any other suitable manner. Basically, however, it is also possible to omit any active thorough mixing of the reaction mixture during the course of the reaction since the ammonia gas being released during the course of reaction of the reactants and also boiling reaction components, such as in particular aniline, also lead to thorough mixing.

The ammonia gas which is evolved during reaction of the reactants is isolated and taken to further recycling or to a controlled waste disposal procedure. Isolation of the ammonia gas being evolved during the course of reaction of the reactants takes place generally with the help of suitable condensers which are known to a person skilled in the art, and the operating conditions are selected in such a way that they enable passage of the ammonia gas while the reactants and reaction products which boil at a considerably higher point are held back in the reaction region.

In addition to the chosen reaction conditions and equipment requirements which have been mentioned, the duration of the reaction according to the invention for preparing N-phenyl-1-naphthylamine is critical for the targeted degree of conversion of the reactants aniline and 1-naphthylamine. Since the process according to the invention for preparing N-phenyl-1-naphthylamine enables recycling of unreacted aniline and/or 1-naphthylamine, the reaction time can be varied between wide limits and can be chosen from a process/economic point of view, for example, in such a way that the space time yields of the reaction part of the process according to the invention are as high as possible and the cost of separating unreacted starting material for recycling is as small as possible. In general more than 50%, preferably more than 60%, in particular more than 70% of the 1-naphthylamine introduced into a discrete reaction batch or, for continuous procedures, into the reaction core is converted.

The mixture produced after terminating the reaction, preferably after cooling to a temperature of less than 100° C., is initially treated with water and/or an aqueous solution of recovered catalyst mixture from preceding processes and thoroughly mixed. The two-phase mixture produced in this way is then taken to a phase separation process. The amount of water used and/or, in the case of fluorine containing catalysts, the aqueous solution of catalyst mixture recovered from preceding working up processes used is preferably chosen in such a way that the aqueous extract produced after the final phase separation process mentioned above contains about 1–35% of non-volatile catalytically-active components. The temperature of the two-phase mixture is generally maintained within the range between 40 and 100° C. during the course of extraction and phase separation.

The organic phase obtained after the phase separation procedure mentioned above is preferably subjected to further extraction. Basically, however, it is also possible to distill this without any further treatment. The second extraction is performed with water to which is optionally added between 0 and 50%, preferably between 5 and 30%, in particular between 10 and 20% of one or more auxilliary agents, preferably one or more salt like inorganic auxilliary agents, in particular one or more substances from the group of alkali metal and alkaline earth metal halides, alkali metal sulfates, alkali metal carbonates and alkali metal hydrogen carbonates. The temperature of the two-phase mixture during the course of extraction and phase separation is generally maintained within the range between 30 and 90° C. In the event that iodine or iodine containing catalyst mixtures are used, it may be advisable to perform the second extraction step in the presence of water-soluble, salt like compounds which are able to bond iodine residues or to convert these by reduction to water-soluble iodide. Sodium sulfite, sodium bisulfite, sodium thiosulfate or sodium dithionite may be mentioned by way of example. The two-phase mixture produced during the second extraction step mentioned above is taken to a phase separation procedure. The aqueous phase obtained after phase separation is either recycled for further extraction, or removed and taken to a recovery procedure or to controlled waste disposal. The organic phase obtained after phase separation is separated by distillation. This separation by distillation is performed with the assistance of conventional distillation equipment and distillation techniques which are known to a person skilled in the art in such a way that unreacted aniline and 1-naphthylamine present in the crude distillation mixture are fully recovered and are reused in subsequent reactions for preparing N-phenyl-1-naphthylarnine.

EXAMPLES

Example 1

A mixture of 279.40 g (3.00 mol) of aniline and 239.97 g (1.68 mol) of 1-naphthylamine are initially introduced into a high pressure autoclave made of V4A which is fitted with an intensive condenser and has a pressure retaining valve beyond the condenser. To this mixture is added 10.37 g of a 21% strength solution of ammonium tetrafluoroborate in water. The mixture is initially heated under atmospheric pressure to a temperature of about 100° C., wherein about 5–15 g of a mixture of aniline and water is distilled off. Then the mixture is heated to 280° C., wherein the pressure increase beyond the condenser is restricted to 3 bar by means of the pressure retention valve. Boiling aniline is prevented from evaporating by the intensive condenser, whereas the ammonia gas which is produced is allowed to escape via the pressure retention valve as the pressure rises. Samples are removed from the autoclave at regular intervals and analysed by gas chromatography.

| Reaction time [min] | Aniline [wt. %] | 1-naphth-yl-amine [wt. %] | N-phenyl-1-naph-thyl-amine [wt. %] | Di-phenyl-amine [wt. %] | Conversion of 1-naphthyl-amine [%] | Yield of N-phenyl-1-naphth-yl-amine [%] |
|---|---|---|---|---|---|---|
| 0   | 50.0 | 45.0 | 1.9  | 0.07 | 0.6  | 2.8  |
| 60  | 40.0 | 27.1 | 24.6 | 0.32 | 40.3 | 35.4 |
| 180 | 31.5 | 11.3 | 49.0 | 0.10 | 75.1 | 70.7 |
| 300 | 28.6 | 5.5  | 59.1 | 0.05 | 87.9 | 85.1 |
| 420 | 27.6 | 4.1  | 61.3 | 0.01 | 91.1 | 88.4 |
| 660 | 26.7 | 2.5  | 61.9 | 0.02 | 94.4 | 89.3 |
| 900 | 26.5 | 2.1  | 64.2 | 0.01 | 95.3 | 92.6 |

Example 2 (for comparison)

The reaction was performed in the same way as in example 1, but without a pressure retention valve, at atmospheric pressure and 210° C.

| Reaction time [min] | Aniline [wt. %] | 1-naphth-yl-amine [wt. %] | N-phenyl-1-naph-thyl-amine [wt. %] | Di-phenyl-amine [wt. %] | Conversion of 1-naphthyl-amine [%] | Yield of N-phenyl-1-naphth-yl-amine [%] |
|---|---|---|---|---|---|---|
| 0   | 48.3 | 44.7 | 3.6  | 0.03 | 1.4  | 5.1  |
| 93  | 41.2 | 34.7 | 19.2 | 0.02 | 23.3 | 27.7 |
| 213 | 34.4 | 24.2 | 35.2 | 0.12 | 46.6 | 50.7 |
| 356 | 32.1 | 19.1 | 43.4 | 0.02 | 57.9 | 62.6 |
| 453 | 31.2 | 17.0 | 45.7 | 0.02 | 62.6 | 65.9 |
| 693 | 30.4 | 14.9 | 48.7 | 0.01 | 67.2 | 70.2 |
| 933 | 29.3 | 13.0 | 51.2 | 0.02 | 71.3 | 73.8 |

Example 3

2,550 kg (27.4 kmol) of aniline and 2,180 kg (15.2 kmol) of 1-naphthylamine were introduced to a high pressure autoclave made of V4A, which was provided with a condenser, a coiled condenser connected in series and beyond that a pressure retention valve. To this solution were added 88 kg of an approximately 21% strength of an aqueous catalyst solution which had been prepared from aniline, boric acid and aqueous hydrofluoric acid. The reaction mixture was heated under reflux within 7 hours to 200° C. and during the course of further reaction to 250° C. within 30 hours. Heating was performed in a controlled manner so that only small amounts of a mixture of ammonia, aniline and water constantly distilled off via the head, while the rise in pressure due to the ammonia gas being produced was restricted by means of the pressure retention valve set at 2.5 $bar_{abs}$ connected beyond the cooling system.

After 41 hours, reaction had terminated. The reaction mixture had the following composition after 31, after 35 and after 41 hours, this being determined using gas chromatography on samples which had been withdrawn at these times.

| Hours | Aniline [%] | 1-NA [%] | PAN [%] | Yield of PAN [% of th.] | DNA [%] | DPA [%] | Conversion of 1-NA [%] |
|---|---|---|---|---|---|---|---|
| 31 | 45.90 | 12.50 | 37.50 | 52.0% | 3.10 | 0.11 | 73.5% |
| 35 | 34.50 | 10.40 | 50.00 | 69.3% | 4.40 | 0.12 | 77.9% |
| 41 | 27.00 | 6.50 | 60.70 | 84.1% | 5.00 | 0.15 | 86.2% |

PAN = N-phenyl-1-naphthylamine
1-NA = 1-naphthylamine
DNA = Di-(1-naphthylamine)
DPA = Diphenylamine The mixture was worked up by extraction and multi-stage distillation.

What is claimed is:

1. A process for batchwise or continuous preparation of N-phenyl-1-naphthylamine by reacting aniline and 1-naphthylamine in the condensed phase at 100–400° C., characterised in that the reaction is performed in the presence of a catalyst and at a reaction pressure which is higher than atmospheric pressure.

2. The process according to claim 1, characterized in that the reaction is performed at a pressure in the range of from above atmospheric pressure up to 15 bar.

3. The process according to claim 1 characterized in that the reaction is performed at 150 to 350° C.

4. The process according to claim 1 characterized in that the reaction is performed in the presence of a catalyst mixture obtained by reacting hydrogen fluoride, boric acid and at least one of the compounds selected from aniline and 1-naphthylamine.

5. A process according to claim 4, characterised in that the reaction is performed in the presence of a catalyst from the group methane- and ethanesulfonic acid, benzenesulfonic acid, p-toluenesulfonic acid, 4-chlorobenzenesulfonic acid, 4bromobenzenesulfonic acid, 2-sulfobenzoic acid, o-, m- and p-aminobenzenesulfonic acid.

6. The process according to claim 1 characterized in that, after terminating the reaction, extraction of the product mixture obtained is performed using water or an aqueous solution in order to isolate the catalytically active components.

7. The process according to claim 1 characterized in that 1-naphthylamine or a mixture of 1-naphthylamine with 5 to 40% of the entire amount of aniline to be used is added to the reaction vessel, after initially introducing the remaining aniline and the catalyst, during or after heating to the chosen temperature and after adjusting to the selected pressure.

8. The process of claim 1 in which the reaction is conducted at a pressure of from 1.5 to 10 bar.

9. The process of claim 1 in which the reaction is conducted at a pressure of from 1.5 to 5 bar.

10. The process of claim 9 in which the reaction is conducted at a temperature of from 180 to 300° C.

11. The process of claim 1 in which the reaction is conducted at a temperature of from 180 to 300° C.

12. The process of claim 1 in which the catalyst is a mixture of salt-like components represented by the formula $$AX \qquad (II)$$

in which

A represents an $H^+$, $NH_4^+$, phenyl-$NH_3^+$, (1-naphthyl)-$NH_3^+$, phenyl-$NH_2$-phenyl$^+$, or phenyl-$NH_2$-(1-naphthyl)$^+$ cation, and X represents an anion corresponding to the formula $$B(OH)_nF_{4-n}$$

in which n represents an integer of from 0 to 4.

13. The process of claim 12 in which

A represents an $NH_4^+$ and/or phenyl-$NH_3^+$ cation and

X represents the anion $BF_4^-$.

14. The process of claim 12 in which the catalyst is $NH_4^+BF_4^-$ and/or phenyl-$NH_3^+BF_4^-$.

15. The process of claim 1 in which the reaction is conducted in the presence of a catalyst selected from monosulfonic acids, disulfonic acids, and trisulfonic acids.

16. The process of claim 1 in which the reaction is conducted in the presence of a catalyst selected from monosulfonic acids and disulfonic acids.

17. The process of claim 1 in which the reaction is conducted in the presence of a catalyst corresponding to the formula $$R\text{—}(SO_3H)_n \qquad (III)$$

in which

R represents a straight chain $C_1$–$C_{20}$ alkyl group, a branched $C_1$–$C_{20}$ alkyl group, phenyl group, substituted phenyl group having up to three substituents, naphthyl group, substituted naphthyl group having up to three substituents, pyridinyl group, substituted pyridinyl group having up to three substituents, in which any substituent present is selected from $C_1$–C6 straight chain alkyl groups, branched $C_1$–$C_6$-alkyl groups, halogen, amino, straight-chain or branched $C_1$–$C_6$-alkyl amino groups, di-($C_1$–$C_6$-alkyl) amino groups, hydroxyl, straight-chain or branched $C_1$–$C_6$-alkoxy or carboxyl groups and n represents 1, 2 or 3.

18. The process of claim 17 in which any substituent present in the R group is selected from straight-chain $C_1$–$C_4$ alkyl groups, branched $C_1$–$C_4$ alkyl groups, fluorine, chlorine, bromine, amino and hydroxyl groups.

19. The process of claim 17 in which any substituent present in the R group is selected from a methyl group, chlorine, bromine, amino groups, hydroxyl groups and carboxyl groups.

* * * * *